United States Patent [19]

Mohanty et al.

[11] Patent Number: 5,574,844

[45] Date of Patent: Nov. 12, 1996

[54] COMPUTER SYSTEM AND METHOD FOR PROCESSING ATOMIC DATA TO CALCULATE AND EXHIBIT THE PROPERTIES AND STRUCTURE OF MATTER

[75] Inventors: Ajaya K. Mohanty, Red Hook; Farid A. Parpia, Lake Katrine, both of N.Y.

[73] Assignee: International Business Machines Corporation, Armonk, N.Y.

[21] Appl. No.: 310,459

[22] Filed: Sep. 22, 1994

[51] Int. Cl.$^6$ ................................................ G06F 15/00
[52] U.S. Cl. .................. 395/326; 395/348; 395/340; 395/352; 364/496; 364/497; 364/498; 364/499
[58] Field of Search .................................. 395/161, 159, 395/157, 156, 155, 147; 364/496, 497, 498, 499

[56] References Cited

U.S. PATENT DOCUMENTS

| | | | |
|---|---|---|---|
| 5,249,137 | 9/1993 | Wilson et al. | 364/496 |
| 5,386,507 | 1/1995 | Teig et al. | 395/161 |

OTHER PUBLICATIONS

Parpia, F. A. et al., "Relativistic basis-set calculations for atoms with Fermi nuclei", *Physical Review A* ©1992 The American Physical Society(, vol. 46, No. 7, 1 Oct. 1992, pp. 3735-3745.

Parpia, F. A. et al., "Integral Generation For Relativistic Multiconfiguration Dirac-Fock Calculations Using Gaussian. Basis Sets", IBM DSD Technical Report, Aug. 14, 1991, pp. 1-10 and cover.

Parpia, F. A. et al., "An Atomic Relativistic Multiconfiguration Self-Consistent-Field Method Using Gaussian Basis Sets", *IBM DSD Technical Report KGN-276*, May 30, 1991, pp. 1-32, cover and Corrigendum.

*Primary Examiner*—Raymond J. Bayerl
*Assistant Examiner*—A. Katbab
*Attorney, Agent, or Firm*—Floyd A. Gonzalez; Michaelson & Wallace

[57] ABSTRACT

A computer technique for providing a user-friendly environment which simplifies the construction of relativistic models of atoms and ions. A computer includes a data processing system, a visual display unit and a data entry device. An operating system, a text/graphic interactive user interface and a number of atomic structure programs reside in the data processing system. The atomic structure programs perform atomic computations to calculate and construct mathematical atomic models based on specific atomic data which is input by an operator and retrieved from a stored atomic data base. The text/graphic interactive user interface includes the following programs: SMARTPET (SMART PEriodic Table tool), ATOMGRAF (ATOMic GRAph(F)ics), RASPIE (Relativistic Atomic Structure Program Interactive Environment), and ATOMBAS (ATOMic data BASe). SMARTPET presents atomic data in familiar formats so that a user can select and identify the atom or ion to be investigated. RASPIE provides a windows-based interactive environment for communication between the user and the atomic structure programs. RASPIE furnishes the input-output (I/O) requirements of atomic structure programs. ATOMGRAF generates graphical quantitative plots of the output results of atomic structure programs. ATOMBAS is a data base storing information for the construction of atomic models for basis set programs.

11 Claims, 9 Drawing Sheets

| GDFB BASIS INPUT | | 360 |

$^{138}_{56}$Ba

Barium

Neutral Barium: Chakravorty basis set.   361

| | |
|---|---|
| NSYM | 5 |
| (IOCS(I), I = 1,NSYM) | 6 4 4 2 2 |
| ATW, ZN | 0.0 56.0 |
| CMULT, LBREIT | 3 .FALSE. |
| IREAD, GENCLF, NCYCLE, THRESH | 0 .FALSE. 30 1.0D-06 |
| ALFAO, BETA | 0.00500392 1.97764820 |
| NDBASF | 32 32 32 32 32 |
| IDSTR | 1 1 1 1 1 |

EXIT   HELP

FIG. 8

COMPUTER SYSTEM AND METHOD FOR PROCESSING ATOMIC DATA TO CALCULATE AND EXHIBIT THE PROPERTIES AND STRUCTURE OF MATTER

BACKGROUND OF THE INVENTION

1. Field of the Invention

The invention relates to data processing systems and methods and, particularly, to windows-based software tools for providing a user-friendly environment for the calculation and visualization of atomic electronic structure.

2. Description of the Prior Art

Scientists, engineers and other practitioners in the natural sciences often use a conventional data processing system having one or more atomic structure programs for constructing mathematical models of atoms and ions. These mathematical models are of interest in themselves; they are also the first step in the construction of mathematical models of other forms of matter such as molecules and solids. A typical user of such programs would be, for example, a biochemists in a pharmaceutical firm who may employ several atomic structure programs along with other molecular-modeling techniques in designing new drugs and simulating their effects. Three popular prior art atomic structure programs are the GDFB, REATOM, and MCGDFB programs. These programs are discussed in the following publications: Parpia, F. A., and Mohanty, A. K., "An Atomic Relativistic Multiconfiguration Self-Consistent-Field Method Using Gaussian Basis Sets," May 30, 1991 *IBM DSD Technical Report KGN*-276; Parpia, F. A., and Mohanty, A. K., "Integral Generation for Relativistic Multiconfiguration Dirac-Fock Calculations Using Gaussian Basis Sets," Aug. 14, 1991 *IBM DSD Technical Report*; and Parpia, F. A., and Mohanty, A. K., "Relativistic basis-set calculations for atoms and Fermi nuclei," *Physical Review A*, Volume 46, Number 7, Oct. 1, 1992, pp. 3735–3745.

To use these and similar programs, the user must input complicated forms of standard atomic data related to the elements being investigated. Such atomic data are usually obtained from a variety of sources such as scientific encyclopedias, chemical handbooks, professional journals, and the like. After collecting the data, the user must then format it for input to the particular atomic structure programs being used. Next, the user inputs the formatted data, runs the programs and generates the needed output information.

Although existing atomic structure programs have served the purpose, they have not proved entirely satisfactory because they generally have cumbersome user interfaces. Users of these programs, such as the GDFB, REATOM, and MCGDFB programs, cited above, often expend much effort in preparing the program inputs and analyzing the execution results. A typical program user manually enters the program inputs from a conventional computer keyboard. Additionally, the outputs or execution results of prior art programs usually comprise complicated data lists which require extensive analysis for proper interpretation and subsequent use. Consequently, there has been a long recognized need for improved user interfaces that make the tasks involved in the use of atomic structure programs easier and quicker to perform. Our present invention fulfills this need.

SUMMARY OF THE INVENTION

Our invention is a computer technique for providing a user-friendly environment which simplifies the construction of mathematical atomic models of atoms and ions. To attain this, we contemplate a unique text/graphic user interface tool that permits a user to interact with and perform operations on one or more atomic structure programs. The user interface includes an atomic data base and a graphic display program for displaying graphical representations of mathematical atomic models on a visual display unit.

In general, the invention includes a computer technique for selectively exhibiting the properties and structure of matter. The technique involves the use of a computer having a visual display unit, a data entry device and a data processing system. An atomic structure program for constructing mathematical atomic models resides in the data processing system. Also resident in the data processing system is a text/graphic interactive user interface that permits a user to interact with and perform operations on the atomic structure program via the data entry device and the visual display unit. The user interface also includes a graphic display for displaying graphical representations of the mathematical atomic models on the visual display unit.

More specifically, the invention is directed to systems and methods using a computer apparatus having a data processing system, a display monitor, a mouse and a keyboard. An operating system, a text/graphic interactive user interface and a number of relativistic atomic structure programs reside in the data processing system. The atomic structure programs perform atomic computations to calculate and construct mathematical atomic models based on specific atomic data which is input by an operator and retrieved from a stored atomic data base residing in the data processing system. The text/graphic interactive user interface, which provides a user-friendly environment for communicating with the atomic structure programs, includes the following programs: SMARTPET (SMART PEriodic Table tool), ATOMGRAF (ATOMic GRAph(F)ics), RASPIE (Relativistic Atomic Structure Program Interactive Environment), and ATOMBAS (ATOMic data BASe). SMARTPET presents atomic parameters in familiar formats so that a user can identify and select the atom or ion to be investigated. RASPIE provides a windows-based interactive environment for communication between the user and the atomic structure programs. RASPIE furnishes the input-output (I/O) requirements of the atomic structure programs. ATOMGRAF generates graphical quantitative plots of the output results of the atomic structure programs. ATOMBAS is an atomic data base that stores information for use in the construction of the atomic models.

BRIEF DESCRIPTION OF THE DRAWINGS

The teachings of our invention can be readily understood by considering the following detailed description in conjunction with the accompanying drawings, in which:

FIGS. 7, 8 and 9 are diagrammatic illustrations of various window configurations generated and displayed by RASPIE in accordance with the FIG. 6 flow diagram.

DETAILED DESCRIPTION OF THE PREFERRED EMBODIMENT

Figure 1:
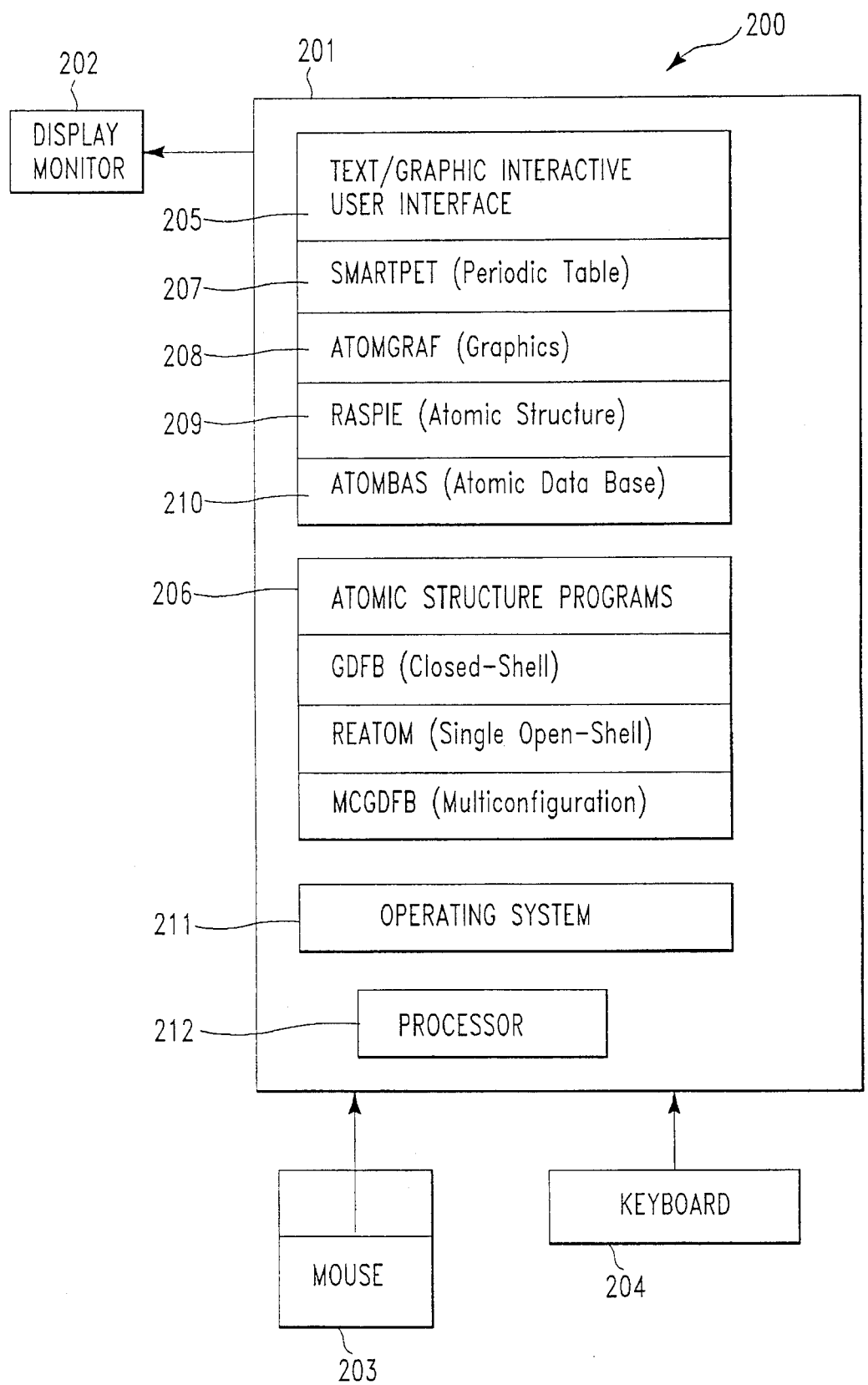
FIG. 1 is a block diagram of a computer system constructed in accordance with a preferred embodiment of the invention.

Referring now to the drawings, FIG. 1 shows computer 200 having data processing system 201 with processor 212. Data processing system 201 connects to display monitor 202, mouse 203, and keyboard 204 in a conventional manner. Operating system 211, text/graphic interactive user interface 205 and atomic structure programs 206 reside in data processing system 201.

Atomic structure programs 206 include three well known applications programs capable of making atomic computations. Specifically, atomic structure programs 206 include the GDFB, REATOM, and MCGDFB programs which were discussed above and are chosen here for illustrative purposes only. Other programs capable of making atomic computations are available in the art and may be substituted for one or more of the three illustrative programs disclosed herein.

Atomic structure programs 206 exemplify typical computer programs which calculate and construct mathematical atomic models based on specific atomic input data. As stated above, because atomic input data is usually complex in both form and substance, program users often find such data difficult to manually assemble and input accurately. Text/graphic interactive user interface 205 includes four windows-based programs which provide a user-friendly environment in which an operator can more readily communicate with atomic structure programs 206.

Text/graphic interactive user interface 205 includes the following programs: SMARTPET (SMART PEriodic Table tool) 207, ATOMGRAF (ATOMic GRAph(F)ics) 208, RASPIE (Relativistic Atomic Structure Program Interactive Environment) 209, and ATOMBAS (ATOMic data BASe) 210. SMARTPET 207 uses a conventional periodic table of the chemical elements as a starting point for presenting atomic parameters in familiar formats so that a user can identify the atom or ion to be investigated. RASPIE 209 provides a windows-based interactive environment for communication between the user and atomic structure programs 206. RASPIE 209 furnishes the input-output (I/O) requirements of atomic structure programs 206. ATOMGRAF 208 generates graphical quantitative plots of the output results of atomic structure programs 206. ATOMBAS 210 is a data base that stores information for the construction of atomic models for basis set programs. ATOMBAS 210 may include the atomic data base GAUSBAS (GAUSsian dataBASe) which is constructed from even-tempered Gaussian basis functions. The user will be able to update ATOMBAS 210 from calculations performed by RASPIE 209.

Figure 2:
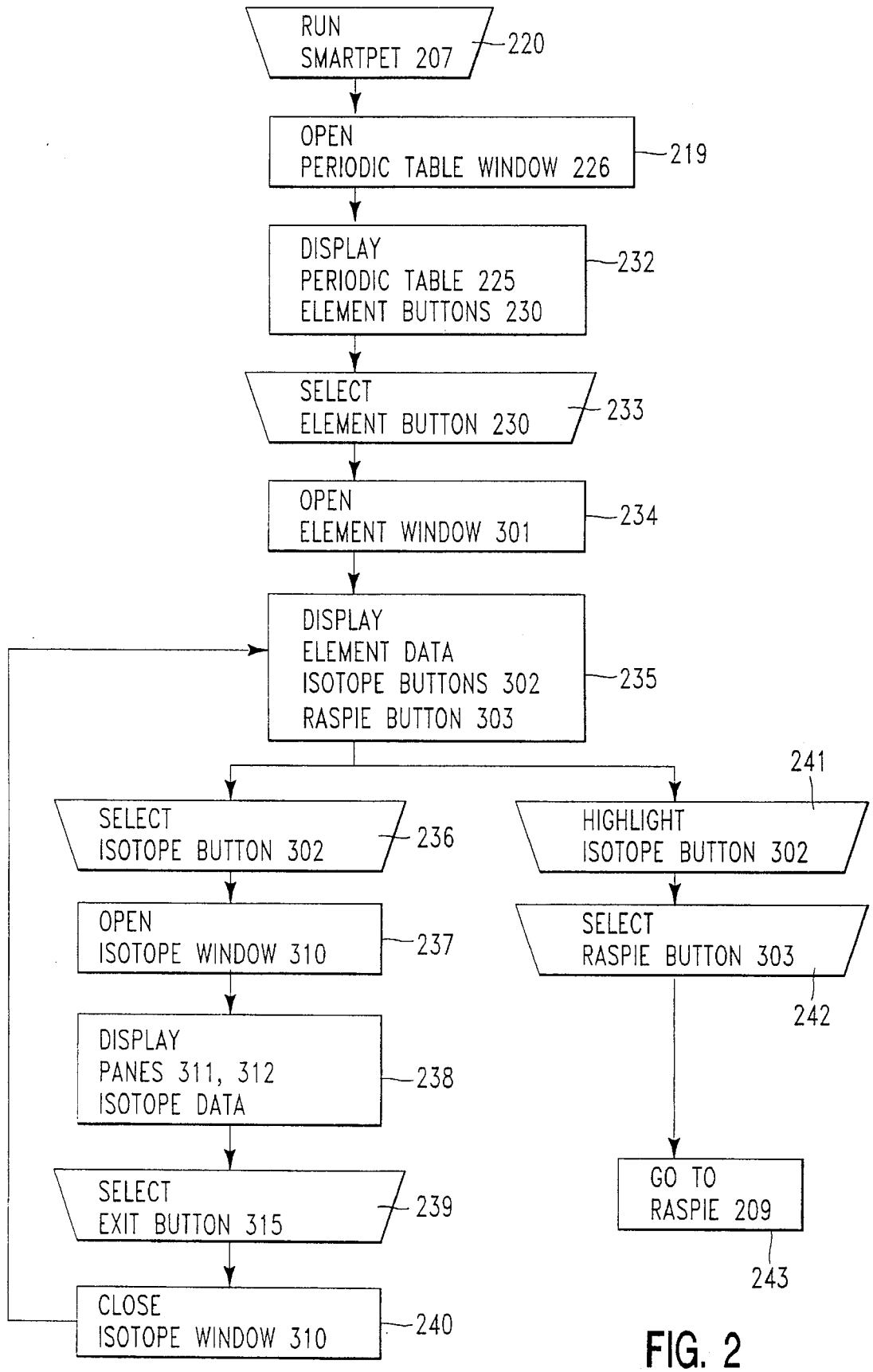
FIG. 2 is a computer flow diagram illustrating the operation of the SMARTPET portion of the preferred embodiment of FIG. 1.
Figure 3:
FIGS. 3–5 are diagrammatic illustrations of various window configurations generated and displayed by SMARTPET in accordance with the FIG. 2 flow diagram.

FIGS. 2–5 illustrate the construction and operation of SMARTPET 207. In run step 220 of FIG. 2, the user initiates the process by running SMARTPET 207. In response, SMARTPET 207 opens PERIODIC TABLE window 226 in open step 219. In display step 232, SMARTPET 207 displays periodic table 225 with element buttons 230 in window 226 as shown in FIG. 3. Window 226 includes a conventional top border having a title bar 221, minimize button 222, maximize button 223, and control box 224. Window 226 further includes conventional EXIT button 227 and HELP button 228. Conventional mouse pointer 231 of mouse 203 appears in window 226.

Periodic table 225, which SMARTPET 207 retrieves from ATOMBAS 210, comprises a set of selectable element buttons 230 aligned in rows and columns to represent a conventional periodic table of the chemical elements. A chemical element abbreviation and its corresponding atomic number label each element button 230. In a standard fashion, periodic table 225 groups chemical elements with similar properties according to a well known periodic law. Table 225 sorts the elements into seven different periods numbered "1" through "7" and into sixteen groups according to certain well known characteristics. The Roman numerals I–VIII, the letters A and B, and ZERO identify the groups. The lanthanide series (elements with atomic numbers 58–71) and the actinide series (elements with atomic numbers 90–103) do not conform to the usual periodic laws; as such, they appear below the main body in two rows. Although periodic table 225 uses the traditional format, other formats are also possible. For example, in some cases a user may prefer a table which sorts the elements by electronic configuration. Such tables are known to those skilled in these arts and may also be used in window 226.

To activate a function via SMARTPET 207, the system user highlights and/or selects buttons 227, 228, and 230 via mouse 203 and its mouse pointer 231, or via keyboard 204 in a conventional manner. It will be assumed for the present discussion that, in general, a single mouse click highlights a button, and a double click selects the button so that its associated function executes. In window 226, for example, double clicking EXIT button 227 closes PERIODIC TABLE window 226, suspends SMARTPET 207, and returns computer control to the operating system 211. Double clicking HELP button 228 opens a help menu that can be used to assist the user with system operation.

Figure 4:
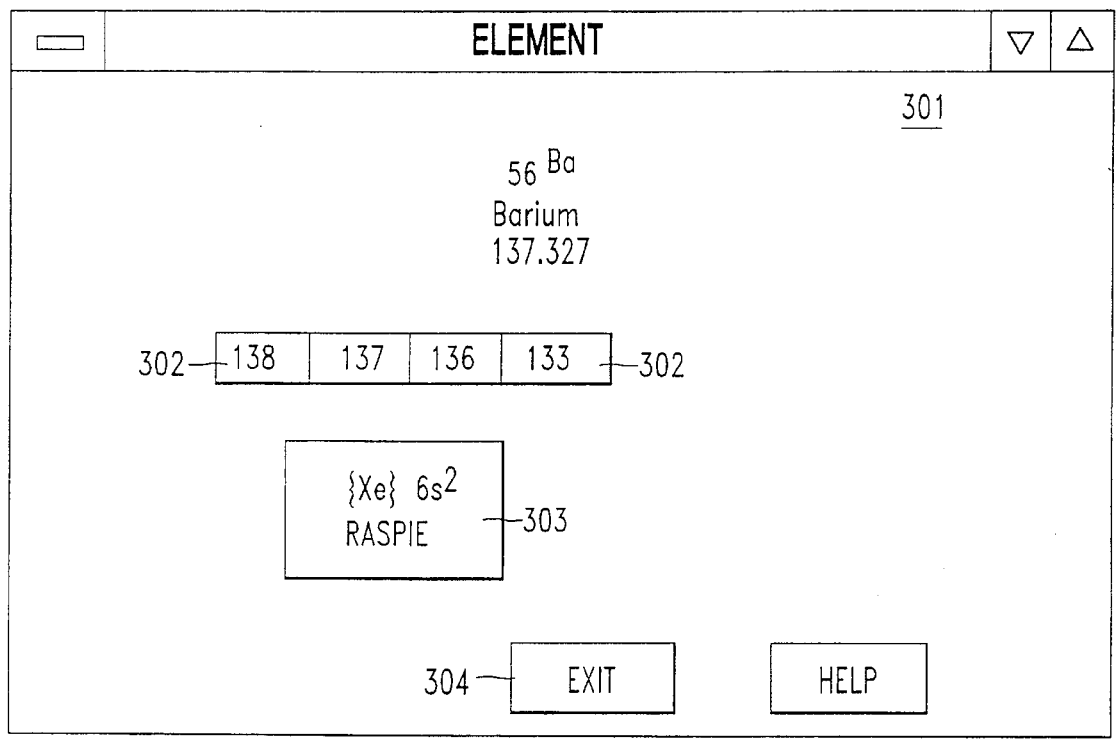

In accordance with the process of FIG. 2, double clicking one of the element buttons 230, select step 233, causes SMARTPET 207 to open ELEMENT window 301, open step 234. ELEMENT window 301, which is illustrated in FIG. 4, may be overlaid on PERIODIC TABLE window 226 or otherwise arranged on display monitor 202 in a conventional manner. Since the techniques of arranging and manipulating windows on a common display are well known, no further discussion of this point will be made. Also for visual clarity, only window 226 of FIG. 3 shows mouse pointer 231.

In display step 235 of FIG. 2, SMARTPET 207 displays in ELEMENT window 301 the set of isotope buttons 302 and RASPIE select button 303. ELEMENT window 301 also contains EXIT button 304, which, when selected (double click), closes ELEMENT window 301 and returns the user to the previous window, i.e. PERIODIC TABLE window 226.

ELEMENT window 301 further contains data related to the element selected in select step 233. SMARTPET 207 retrieves this data from ATOMBAS 210. Specifically, ELEMENT window 301 of FIG. 4 contains an array of atomic data related to the element Barium, which is found in periodic table 225 at the button 230 that is located in Group II-A, Period 6 and labeled: "Ba 56." The atomic data listed in ELEMENT window 301 for Barium includes the element abbreviation, Ba, with a subscript of the atomic number, 56, the element name, Barium, and the average atomic weight, 137.327. The atomic data in FIG. 4 also includes the mass numbers of isotopes of the element Barium. These mass numbers appear as labels on isotope buttons 302. Since the element Barium has four stable isotopes, FIG. 4 depicts four isotope buttons 302 labeled with the corresponding mass numbers: 138; 137; 136; and 133. The displayed atomic data further includes the ground-state configuration of the electron cloud as a label on RASPIE select button 303. For the Barium example shown in FIG. 4, RASPIE select button 303 carries the label "{Xe} 6s$^2$" which is the conventional expression for describing the ground-state configuration of the electron cloud for the Barium isotope identified on button 302.

Figure 5:
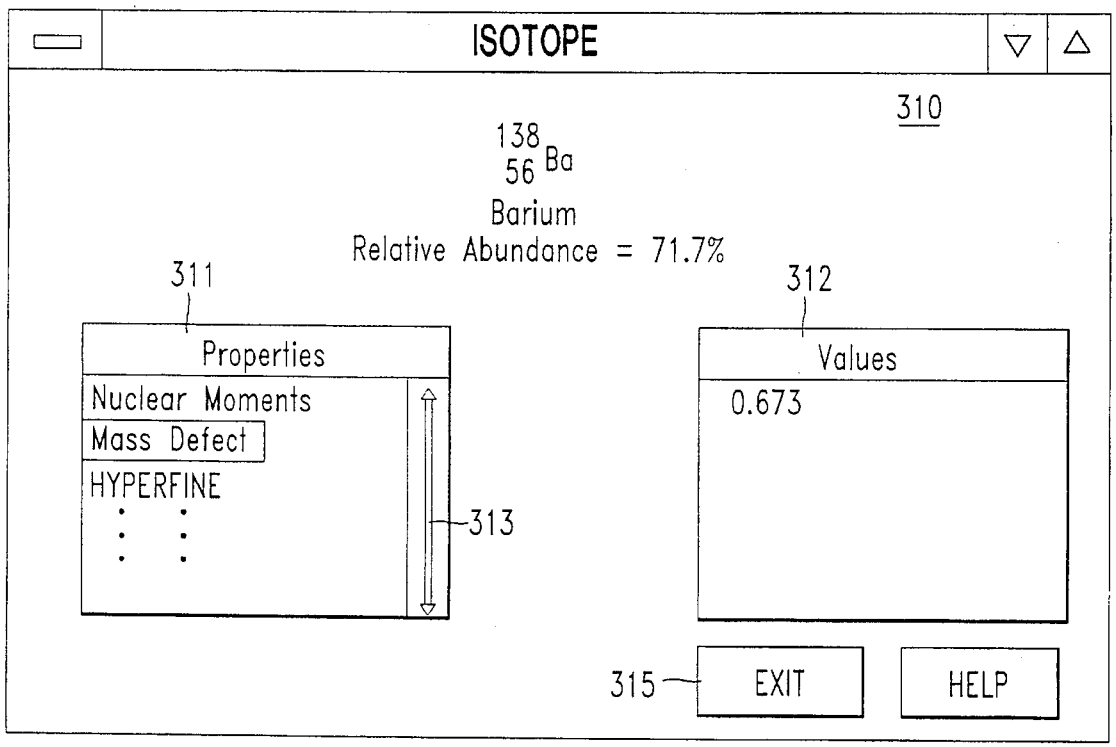

The user may now select (double click) one of isotope buttons 302 in select step 236, or simply highlight (single click) one of isotope buttons 302 in highlight step 241. Selecting one of the isotope buttons 302 causes SMARTPET 207 to first execute open step 237, which opens ISOTOPE window 310, and then executes display step 238, thereby displaying corresponding isotope data from ATOMBAS 210 as seen in FIG. 5. ISOTOPE window 310 contains PROPERTIES window pane 311 and VALUES window pane 312. Window pane 311 contains a listing of the names of atomic properties which the user may highlight one at a time using mouse 203. Window pane 312 contains the associated values of the highlighted property corresponding to the isotope selected in step 236. PROPERTIES window pane 311 includes conventional scroll bar 313 for use in moving throughout the list of properties. PROPERTIES window pane 311 preferably contains an exhaustive list of atomic properties from ATOMBAS 210, such as nuclear moments, mass defect, hyperfine, etc., the values of which the user views in window pane 312 for the purpose of identifying or determining whether or not the selected atom is the one desired. When finished with window 310, the user selects EXIT button 315 in select step 239 of FIG. 2. This action closes ISOTOPE window 310 via close step 240 and returns the user to display step 235.

For the illustrated example in FIG. 5, it is assumed that in select step 236 the user selected (double click) the Barium isotope 138 from ELEMENT window 301 via the isotope button 302 labeled "138," and that the user highlighted (single click) the property "Mass Defect" in window pane 311. As such, ISOTOPE window 310 of FIG. 5 contains the following atomic data: the element abbreviation, Ba; a subscript of the atomic number, 56; a superscript of the mass number, 138; the element name, Barium; the percent of relative abundance for the selected isotope, 71.7%; and, in VALUES window pane 312, the corresponding mass defect value, 0.673, which in atomic units represents the difference between the mass of the Barium isotope 138 and the sum of the masses of its individual components in the free (unbound) state, i.e., the mass defect for the Barium isotope 138.

After the user identifies the element and selects EXIT button 315, SMARTPET returns to display step 235 from which the user can highlight (one click) a desired isotope button 302 via highlight step 241. In select step 242, RASPIE select button 303 is selected (double click), causing the process to proceed to RASPIE 209 via go-to step 243 and run step 320 of FIG. 6.

Figure 6:
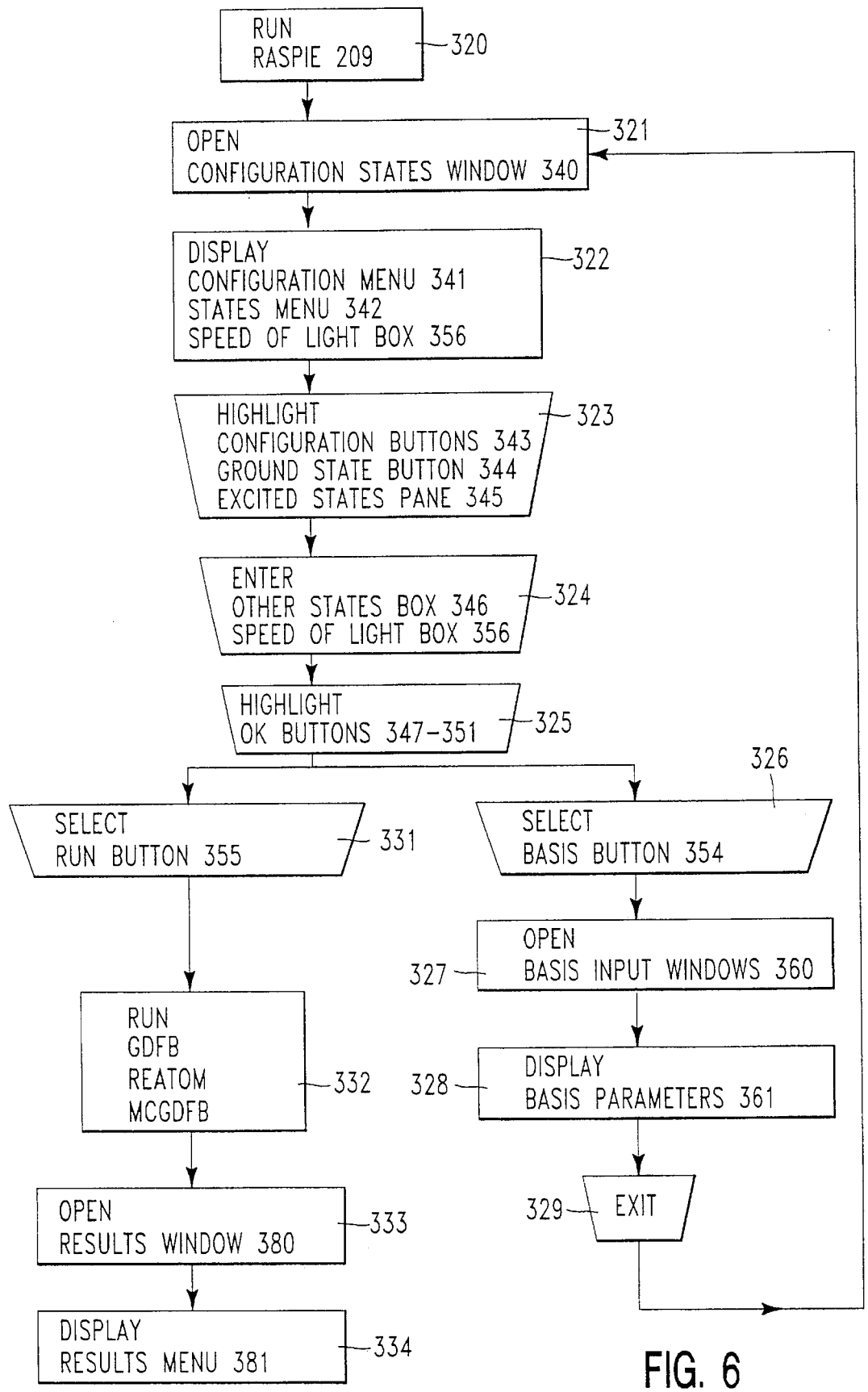
FIG. 6 is a computer flow diagram illustrating the operation of the RASPIE portion of the preferred embodiment of FIG. 1.
Figure 7:
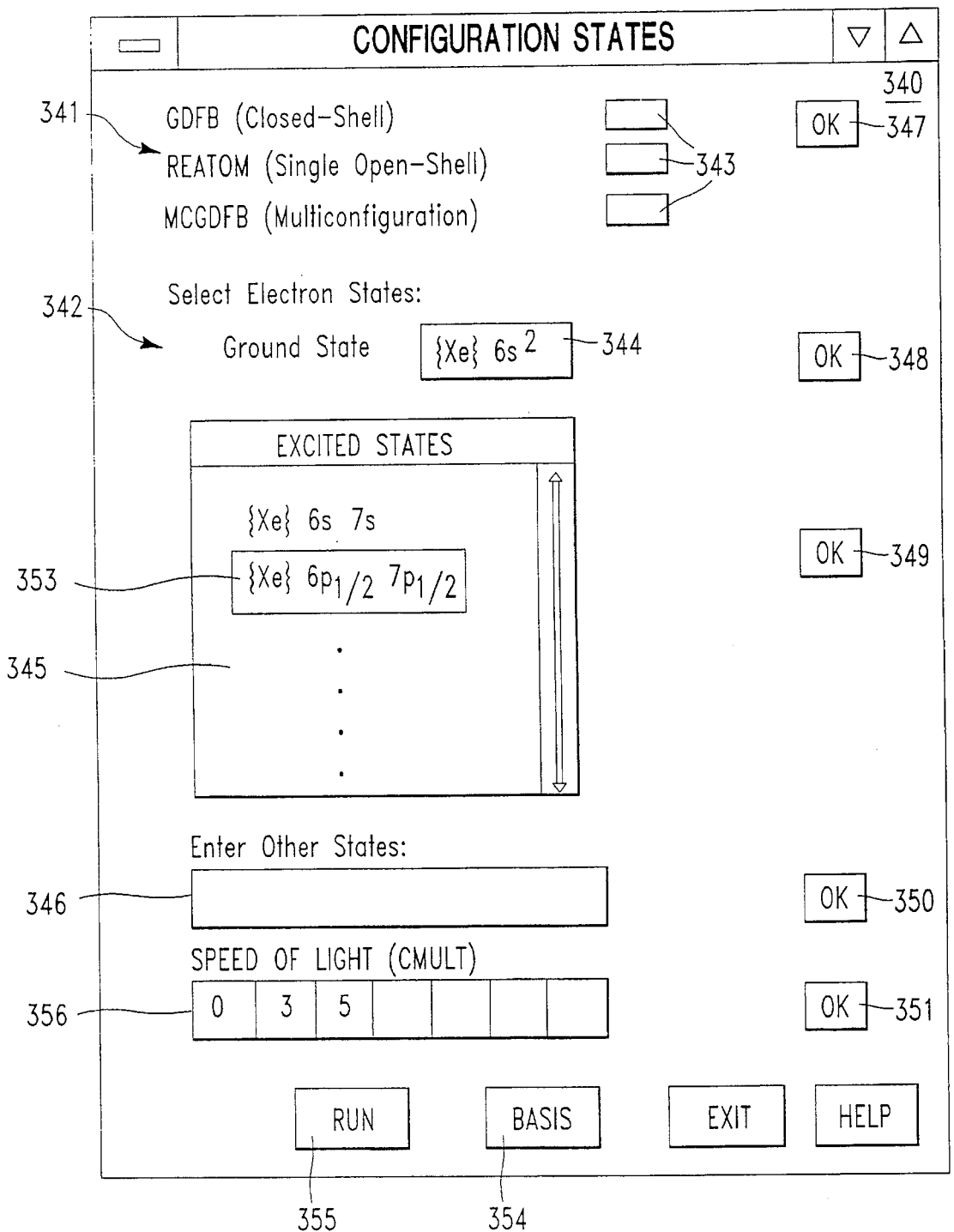

FIGS. 6 and 7 illustrate the construction and operation of RASPIE 209. In run step 320 of FIG. 6, data processing system 201 runs RASPIE 209, which is an interactive environment for investigating relativistic atomic structure. Specifically, RASPIE 209 provides a windows-based interactive environment for communication between the user and atomic structure programs 206. Essentially, RASPIE 209 furnishes the input-output (I/O) requirements of each of the atomic structure programs 206. To accomplish this function, RASPIE 209, in open step 321, opens CONFIGURATION STATES window 340, which displays configuration menu 341, states menu 342 and SPEED OF LIGHT box 356 in display step 322. CONFIGURATION STATES window 340 is illustrated in FIG. 7.

From window 340, the user first chooses, in highlight step 323, one or more of atomic structure programs 206 by highlighting (single click) the corresponding buttons 343. If the user wishes to look at a mathematical model based on a closed-shell configuration, the user chooses the conventional GDFB program by highlighting its button 343. Likewise, if the user wishes to also see a model based on a single open-shell configuration or a multiconfiguration, the user highlights the corresponding buttons 343.

With the desired buttons 343 highlighted, the user next specifies the electron cloud configurations to be used in the calculations performed by the atomic structure programs 206 via highlight step 323 and enter step 324. This process will be illustrated using the ground state of Ba. To choose the ground state configuration, the user simply highlights ground state button 344. The user may also choose one or more excited states from those listed in EXCITED STATES window pane 345. The choices are made in pane 345 by highlighting each of the excited states desired, such as illustrated by highlighter 353. Additionally, the user may sequentially enter other electron state configurations in "OTHER STATES" box 346 via keyboard 204. Finally, as indicated by enter step 324, the user may enter a number of CMULT multiplying factors in SPEED OF LIGHT box 356 via keyboard 204. If no number is entered in box 356, it uses the default value for the speed of light which is 137.0359895 a.u. These factors define different sets of basis parameters 361 that will be used by the atomic structure programs 206 chosen from the configuration menu 341.

After making all desired choices, the user finalizes the choices by highlighting (single click) the appropriate "OK" buttons 347–351 in highlight step 325. The user then causes RASPIE to either display the sets of basis parameters that will be used by the selected atomic structure programs 206 or run the selected atomic structure programs 206.

Specifically, if basis button 354 is selected, via select step 326, from CONFIGURATION STATES window 340 of FIG. 7, RASPIE 209 responds, via open step 327, by opening a number of GDFB BASIS INPUT windows 360 that each display, via display step 328, an appropriate set of basis parameters 361 which are retrieved from ATOMBAS 210 and/or entered by the user. In the present example, three GDFB BASIS INPUT windows 360 are opened, one for each of the three different CMULT multiplying factors, in SPEED OF LIGHT box 356 (viz. 0, 3 and 5). FIG. 8 illustratively shows only one of the three GDFB BASIS INPUT windows 360 (for CMULT=3) that are opened in open step 327. The multiple sets of basis parameters 361 are those that will be used when the selected atomic structure programs 206 are executed via run button 355.

Illustratively, FIG. 8 shows GDFB BASIS INPUT window 360 displaying a list of typical basis parameters 361 for the Barium isotope, which is identified near the top of window 360. To display the specific GDFB BASIS INPUT window 360 on monitor 202, the user, using window 340, performs steps 323–325, i.e. the user chooses GDFB (Closed-Shell) by highlighting the adjacent configuration button 343, highlights ground state button 344, enters the digits 0, 3 and 5 in SPEED OF LIGHT box 356, highlights OK buttons 347 and 348, and selects basis button 354 in select step 326. Because GDFB uses a closed-shell model, the user did not need to select excited states from pane 345 or enter other states via box 346.

The set of basis parameters 361 shown in FIG. 8 specify typical factors for use by GDFB as follows: NSYM specifies the number of symmetries; (IOCS(I), I=1, NSYM) represents the number of shells with symmetry I (the order assumed in GDFB is $s_{1/2}, p_{1/2}, p_{3/2}, d_{3/2}, d_{5/2}, f_{5/2}, f_{7/2}$); ATW is the nuclear mass in atomic mass units (amu); ZN is the atomic number; CMULT is one of the factors entered in SPEED OF LIGHT box 356 which represent the power of ten used by GDFB to obtain the values of the speed of light; LBREIT is .TRUE. if the Breit interaction is to be included self-consistently (i.e., while the orbitals are being calculated), and is .FALSE. otherwise; IREAD specifies the location of the file containing the initial estimates of the eigenvectors and is "0" if GDFB is to generate the estimates; GENCLF is .TRUE. if the coefficient list files are to be generated and .FALSE. otherwise; NCYCLE is the number of self-consistent-field iteration cycles; THRESH is the convergence threshold; ALFAO is the basis set parameter $\alpha_o$; BETA is the basis set parameter $\beta$ (the exponents of the Gaussian basis functions are taken to be contiguous members of the geometric series: $\alpha_i=\alpha_o\beta^{i-1}$, i=1, . . . , n); NDBASF is the number of exponents in the original basis set; and IDSTR is the starting offset of the initial estimate eigenvectors. After viewing the parameters in GDFB BASIS INPUT window 360, the user returns, via exit step 329, to CONFIGURATION STATES window 340.

Figure 9:
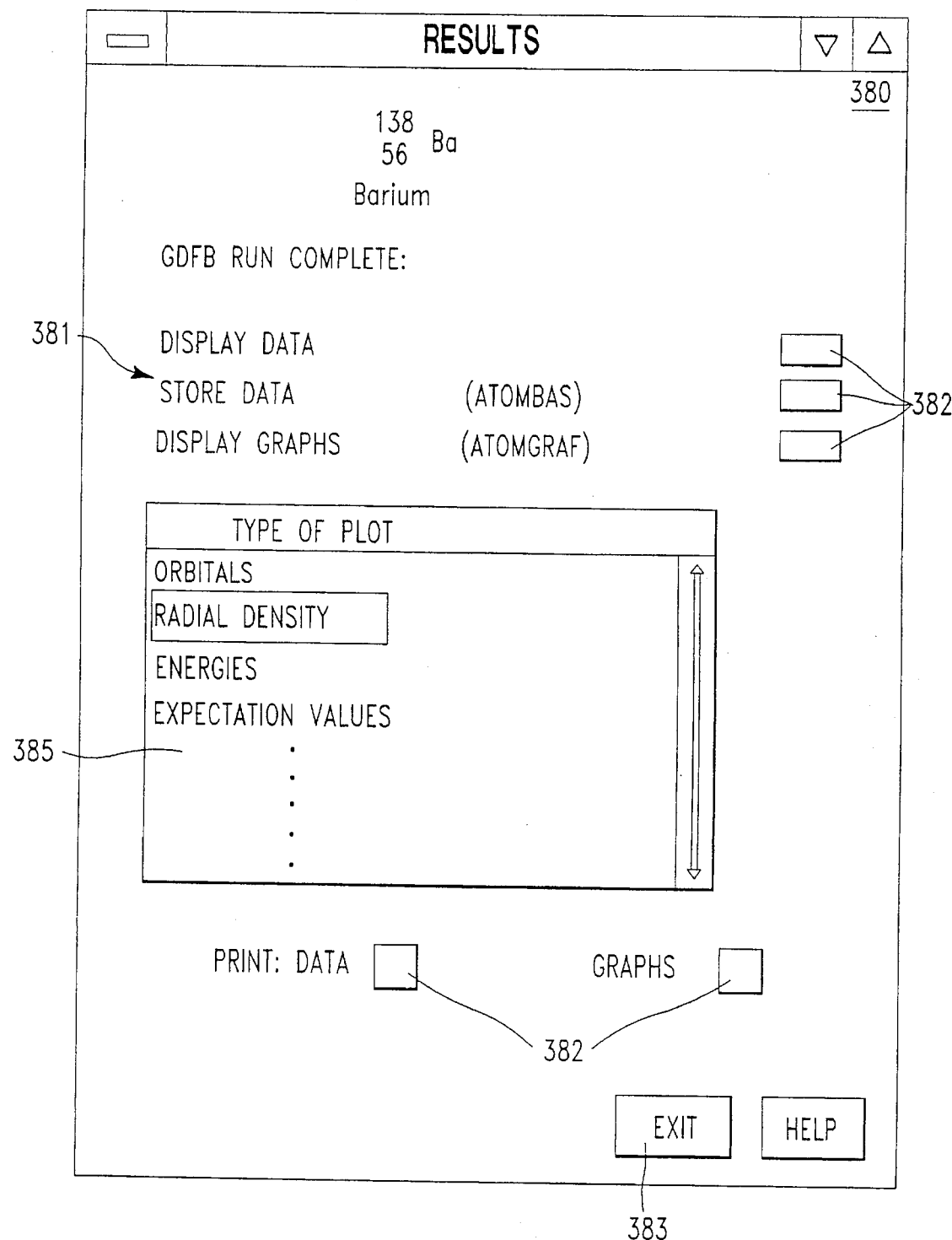

If instead of selecting basis button 354 from CONFIGURATION STATES window 340 of FIG. 7, the user selects run button 355, via select step 331, RASPIE 209 responds by executing the selected atomic structure programs 206, i.e., GDFB, REATOM and MCGDFB, via run step 332. After the appropriate results are calculated by the executed atomic structure programs 206, RASPIE 209 opens RESULTS window 380 of FIG. 9 and displays results menu 381, in open step 333 and display step 334. RESULTS window 380 has radio buttons 382 which permit the user to display the results as data on monitor 202, or to store the results in ATOMBAS 210, or to display the results as graphs via ATOMGRAF 208, or to print the data and/or graphs. The user may return to CONFIGURATION STATES window 340 by selecting EXIT button 383.

If the menu item DISPLAY GRAPHS is selected via button 382, the user will be prompted to select an item from TYPE OF PLOT window pane 385. The radial density function is selected from a number of choices in pane 385 of FIG. 9. ATOMGRAF 208 responds to the users selection of the type of plot by opening and displaying ATOMIC MODEL window 390, which displays curves that represent data plots for the atom being investigated.

Figure 10:
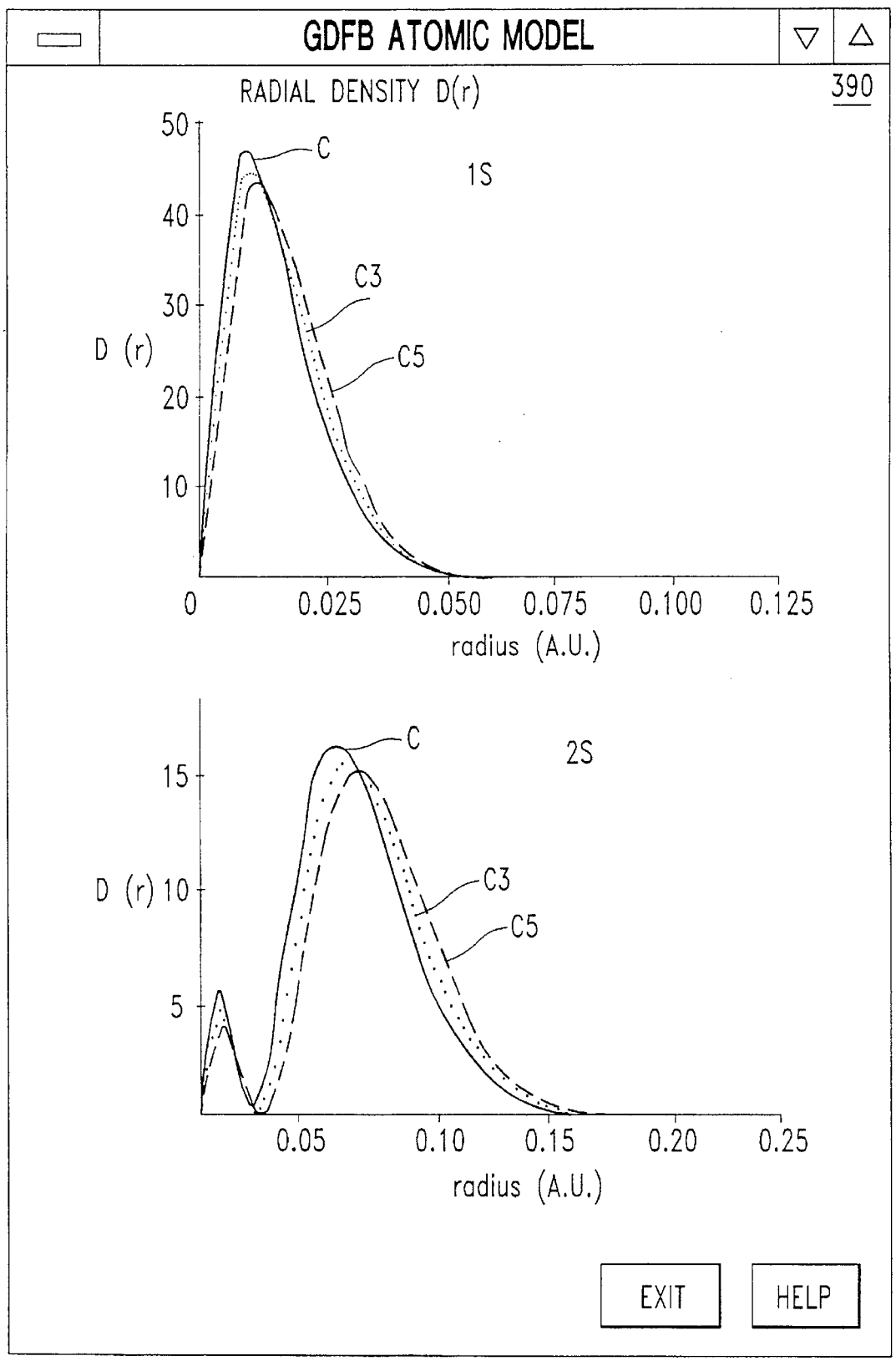
FIG. 10 is a diagrammatic illustration of a window configuration generated and displayed by ATOMGRAF.

Illustratively, ATOMIC MODEL window 390 of FIG. 10 shows two sets of three curves of the normalized radial densities, D(r), for each of the 1s and 2s states of an atom. The solid curves labeled "c" are the full relativistic curves which correspond to CMULT=o in SPEED OF LIGHT box 365. As such, the curves labeled "c" are plotted using the physical value for the speed of light, which is 137.0359895 a.u. The dotted curves labeled "c3", corresponding to CMULT=3, are partial relativistic curves which are plotted using a value for the speed of light which is $10^3$ times the physical value. The dashed curves labeled "c5", corresponding to CMULT=5, are approximations of the nonrelativistic curves which are plotted using a value for the speed of light which is $10^5$ times the physical value. The user can study the relativistic effects on atomic models by comparing the changes in the shapes of the various curves as the value of the speed of light changes from a relatively large number, "c×$10^5$," i.e., the classical nonrelativistic case, to the physical value of the speed of light, i.e., the full relativistic case.

Obviously many modifications and variations of the present invention are possible in the light of the above teachings. For example, it is contemplated that element buttons 230 in FIG. 3 could be color-coded to distinguish between elements that are solids, liquids and gases at room temperature. Likewise, isotope buttons 302 could be color-coded to distinguish between stable and radioactive isotopes. It is also contemplated that ATOMGRAF 208 show a number of different plots, such as quantitative plots of the radial electronic density, orbital wavefunctions, and the three-dimensional density distribution for electrons with spherical symmetry. Further, ATOMGRAF 208 may also provide quantitative Grotrian diagrams of atomic energy levels and bar spectra. Additionally, in accordance with current window technology, the various windows may be simultaneously overlapped on monitor 202 and contain icons that can be dragged across the windows to select, highlight and execute the items. It is to be understood, therefore, that within the scope of the appended claims, the invention may be practiced otherwise than as specifically described.

What is claimed is:

1. A computer apparatus for exhibiting the properties and structure of matter comprising:

a visual display unit;

a data entry device; and a data processing system connected to said visual display unit and said data entry device, said data processing system having atomic structure program means for constructing mathematical atomic models, and a text/graphic interactive user interface having program selection means for permitting a user to interact with and perform operations on said atomic structure program means via said data entry device and said visual display unit, an atomic data base containing atomic information for use by said atomic structure program means for constructing said mathematical atomic models, an atomic data display means for displaying on said visual display unit atomic select buttons and said atomic information in response to selections made by said user via said atomic select buttons and said data entry device, and a graphic display means for displaying graphical representations of said mathematical atomic models on said visual display unit, and wherein said atomic data display means includes a periodic table means for displaying a plurality of said atomic select buttons to form element buttons labeled with said atomic information to form a periodic table of chemical elements on said visual display unit, and an element means for displaying on said visual display unit, in response to selection of one of said element buttons, a plurality of said atomic select buttons to form isotope buttons labeled with isotope information from said atomic information, said isotope information corresponding to the isotopes of said one of said chemical elements.

2. The computer apparatus of claim 1 wherein said atomic data display means further includes isotope means for displaying on said visual display unit, in response to selection of one of said isotope buttons, a properties display means for displaying the values of selected physical properties for the isotope corresponding to said selection of said isotope button.

3. The computer apparatus of claim 1 wherein said element means includes a program selection means button for permitting a user to activate said program selection means via said data entry device.

4. The computer apparatus of claim 3 wherein said program selection means includes program select buttons responsive to activation by a user via said data entry device to activate said atomic structure program means.

5. The computer apparatus of claim 4 wherein said program selection means further includes basis select means for permitting a user to enter and select basis parameters to be used by said atomic structure program means for constructing said mathematical atomic models.

6. The computer apparatus of claim 5 wherein said basis parameters includes the speed of light and said basis select means includes speed of light means for permitting a user to enter a plurality of different values for said speed of light, whereby relativistic effects on said mathematical atomic models may be calculated and displayed.

7. The computer apparatus of claim 6 wherein said program selection means further includes results means for permitting a user to activate said graphic display means for displaying said mathematical atomic models as graphical plots.

8. A computer method for exhibiting the properties and structure of matter on a visual display unit using a data entry device connected to a data processing system having an atomic structure program means for constructing mathematical atomic models, and a text/graphic interactive user interface for permitting a user to interact with and perform operations on said atomic structure program means via said data entry device and said visual display unit, said method comprising the steps of:

storing an atomic data base containing atomic information for use by said atomic structure program means for constructing said mathematical atomic models;

displaying on said visual display unit atomic select buttons and said atomic information in response to selections made by said user via said atomic select buttons and said data entry device;

displaying a plurality of element select buttons labeled with said atomic information to form a periodic table of chemical elements on said visual display unit;

selecting one of said element select buttons via said data entry device and said visual display unit;

displaying on said visual display unit, in response to said selecting of one of said element select buttons, a plurality of isotope select buttons labeled with isotope information from said atomic information, said isotope information corresponding to the isotopes of said one of said chemical elements;

selecting one of said isotope select buttons via said data entry device and said visual display unit;

displaying on said visual display unit, in response to said selecting of one of said isotope select buttons, the values of selected physical properties for the isotope corresponding to said isotope select button; and activating said atomic structure program means to construct said mathematical atomic models corresponding to said isotope select button.

9. The computer method of claim 8 wherein said atomic structure program means uses a set of basis parameters to construct said mathematical atomic models, and further including the step of defining said set of basis parameters by entering some of said basis parameters via said data entry device and said visual display unit and retrieving others of said basis parameters from said atomic data base.

10. The computer method of claim 9 wherein said set of basis parameters includes a plurality of different values for the speed of light, whereby relativistic effects on said mathematical atomic models may be calculated and displayed.

11. The computer method of claim 10 wherein said text/graphic interactive user interface includes a graphic display means, and further including activating said graphic display means via said data entry device and said visual display device for displaying graphical plots of said mathematical atomic models for said isotope select button using said set of basis parameters.

* * * * *